United States Patent [19]

Merianos et al.

[11] Patent Number: 5,122,370
[45] Date of Patent: Jun. 16, 1992

[54] METHOD FOR TREATING ACNE VULGARIS WITH A COMPOSITION CONTAINING A STABLE, HIGH PURITY, SUBSTANTIALLY ANHYDROUS COMPLEX OF PVP-$H_2O_2$

[75] Inventors: John J. Merianos, Middletown; Michael W. Helioff, Westfield, both of N.J.

[73] Assignee: ISP Investments Inc., Wilmington, Del.

[21] Appl. No.: 702,546

[22] Filed: May 20, 1991

[51] Int. Cl.$^5$ .............................................. A61K 33/40
[52] U.S. Cl. ............................ 424/78.05; 424/78.07; 424/78.24; 424/616; 514/859
[58] Field of Search .................. 424/80, 616

[56] References Cited

U.S. PATENT DOCUMENTS

| | | | |
|---|---|---|---|
| 3,376,110 | 4/1968 | Shiraeff | 423/272 |
| 3,480,557 | 11/1969 | Shiraeff | 252/186 |
| 4,163,800 | 8/1979 | Wickett et al. | 514/634 |
| 4,485,091 | 11/1984 | Fitton | 424/62 |

*Primary Examiner*—Leonard Schenkman
*Attorney, Agent, or Firm*—Walter Katz; Marilyn J. Maue; Joshua J. Ward

[57] ABSTRACT

What is provided herein is a method for treating acne vulgaris with a composition containing a stable, high purity, substantially anhydrous complex of PVP and $H_2O_2$ in which the constituents are present respectively in substantially a 1:1 molar ratio and the complex is a free-flowing, fine white powder.

9 Claims, No Drawings

METHOD FOR TREATING ACNE VULGARIS WITH A COMPOSITION CONTAINING A STABLE, HIGH PURITY, SUBSTANTIALLY ANHYDROUS COMPLEX OF PVP-$H_2O_2$

BACKGROUND OF THE INVENTION

1. Field of the Invention

This invention relates to a method for reducing the microbial content of surfaces, and more particularly, to compositions containing a stable, high purity, free-flowing, substantially anhydrous complex of PVP-$H_2O_2$ for treating acne vulgaris.

2. Description of the Prior Art

Stabilized $H_2O_2$ compositions have found wide utility in commercial and industrial applications, e.g. as antiseptics, disinfectants, sterilization agents, bleaching materials, washing concentrates, etchants, in cosmetic preparations, and as a catalyst in polymerizations requiring a free radical source. In biological applications which require an antiseptic, disinfectant or sterilization agent, such $H_2O_2$ compositions require release of an effective amount of oxygen at a desired rate.

Shiraeff, in U.S. Pat. Nos. 3,376,110 and 3,480,557, reacted hydrogen peroxide and PVP in an aqueous solution of the components. The process involved mixing predetermined amounts of PVP and a large excess of aqueous $H_2O_2$, e.g. 50% aqueous solutions, and evaporating the solution to dryness. The Shiraeff composition was described as not necessarily anhydrous due to the hydrophilic nature of the PVP and the water present in the reaction solution. Shiraeff stated that water could be tolerated, however, if it did not affect the solid dry characteristics of the complexes. The $H_2O_2$ content of the composition was given as being at least 2%, and preferably 4.5 to 70% by weight. Prolonged drying of the composition in an attempt to reduce the water content, however, resulted in loss of $H_2O_2$ from the complex, forming a brittle, transparent, gummy, amorphous product of non-reproducible consistency. The resultant hard, brittle chips had a variable $H_2O_2$ content ranging from about 3.20 to 18.07% by weight, depending upon the drying times, and a considerable amount of water.

The Shiraeff PVP-$H_2O_2$ material did not attain commercial success because the product (1) was not a free-flowing powder; (2) its water and peroxide content varied widely; (3) it had consistency and reproducibility problems; and (4) the aqueous laboratory process could not be scaled up due to great loss of $H_2O_2$ during drying.

Acne vulgaris is an inflammatory disease of the pilosebaceous glands characterized by an eruption of the skin, often pustular in nature but not suppurative. Acne is a common affliction of the adolescent and affects a small but significant percentage of the adult population. Acne lesions are of four basic types: comedones (blackheads or whiteheads), papules, pustules, and cysts (or nodules). Various topical agents are utilized in the treatment of acne and these include sulfur, resorcinol, salicylic acid, benzoyl peroxide, vitamin A acid and topical antibiotics. Acne involvement results in unslightly lesions, particularly on the face, and in some cases results in severe scarring.

Accordingly, an object of the invention is to provide a method for treating acne vulgaris with a composition containing a stable, high purity, substantially anhydrous complex of PVP-$H_2O_2$ in a defined molar ratio of 1:1 of constituents and which is a free-flowing, fine white powder.

Another object of the invention is to provide a stick formulation of such composition for treating acne vulgaris in a commercial and consumer-acceptable manner.

Still another object of the invention is to provide a method for reducing the microbial content of skin surfaces afflicted with acne vulgaris with a microbial amount of a 1:1 complex of PVP-$H_2O_2$ having an $H_2O_2$ activity of at least 3%.

SUMMARY OF THE INVENTION

What is provided herein is a method for treating acne vulgaris with a composition containing a stable, high purity, substantially anhydrous complex PVP and $H_2O_2$ in which the constituents are present respectively in substantially a 1:1 molar ratio, and the complex is a free-flowing, fine white powder. This result is accomplished herein in a preferred manner by contacting said surface with a stick formulation containing an antimicrobial amount of such complex.

DETAILED DESCRIPTION OF THE INVENTION

The PVP-$H_2O_2$ complexes of the invention may be prepared by several methods. According to one suitable process, PVP and anhydrous $H_2O_2$ are reacted in predetermined molar ratios in suspension in an anhydrous organic solvent. The product is a uniform, free-flowing, fine white powder which is isolated by filtration from the solvent.

Another method is a suspension process in which water-insoluble PVP is suspended in anhydrous ethyl acetate into which an aqueous, concentrated $H_2O_2$ solution containing about 70 to 85% by weight $H_2O_2$ is slowly added, the amounts of PVP and $H_2O_2$ thereby being reacted corresponding substantially to the desired 1:1 molar ratio in the complex, at a temperature of about 0°–10° C., under agitation. The precipitate obtained is a uniform, free-flowing, fine white powder, which is filtered and dried.

In another method, a fluidized bed of PVP powders which is maintained at a reaction temperature of from about ambient temperature to 60° C., preferably 35°–40° C., is contacted with finely divided droplets of a 30 to 85%, preferably 50–70%, by weight aqueous $H_2O_2$ solution. The feed rate for introduction of the $H_2O_2$ solution suitably is about 5–50 g/minute/kg PVP used, preferably about 15–25 g/minute/kg PVP.

The PVP polymeric starting materials used in the present invention are available commercially as a solid of varying molecular weight, water solubility or insolubility, and water content. Typical water soluble PVP polymers are PVP K-15, PVP C-15, PVP K-29-32, PVP K-30, K-90 and K-120 (GAF Corp.), which contain less than 5% water. Crospovidone is an example of an available water-insoluble PVP material. Mixtures of water soluble and water insoluble PVP also may be used. Preferably water soluble PVP is used herein.

Compositions of the invention suitably contain $H_2O_2$ in an active amount of about 1–10% by weight level, preferably about 3–7%. The active peroxide is present in the 1:1 molar ratio PVP:$H_2O_2$ complex powder in a compatible, non-aqueous, organic solvent, suitably an alcohol or polyol, such as ethanol, propylene glycol, glycerol and the like. Generally the PVP:$H_2O_2$ powder is dissolved in the organic solvent up to the limit of its solubility, and then combined with a base to form the finished product. A stick formulation is preferred because it is easy to apply to the affected area of the skin, and further because it feels comfortable for the user.

Typical active solutions of the 1:1 PVP:$H_2O_2$ powder in the organic solvent include the following:

| ACTIVE COMPONENT OF COMPOSITION | | |
|---|---|---|
| Ex. | Constituent | Amount (g) |
| A | 1:1 PVP:$H_2O_2$ (23.4%) | 60 |
| | Ethanol (100%) | 40 |
| | Active $H_2O_2$ | 14% |
| B | 1:1 PVP:$H_2O_2$ (23.4%) | 50 |
| | Propylene glycol | 50 |
| | Active $H_2O_2$ | 12% |
| C | 1:1 PVP:$H_2O_2$ (23.4%) | 25–30 |
| | Glycerol | 70–75 |
| | Active $H_2O_2$ | 6–7 |

A typical base formulation for a stick formulation is the following:

| Constituent | Amount (g) |
|---|---|
| PEG 4000 | 50. |
| PEG 400 | 5. |
| Stearic Acid | 5. |
| Cetyl alcohol | 5. |
| Synchrowax HRC (glycerol tribenate) | 5. |
| Crodavol PTC (glycerol ester) | 20. |
| Cyclomethicone DC 345 | 5. |
| Talc | 15. |
| | 100. |

Preferably the active component and the base are combined in amounts of about 40-60:60:40, respectively, although higher and lower ratios may be used as well, the result being a well-formulated stick which has an active peroxide content of about 1–10%.

The preferred procedure for formulating the desired anti-acne product is the following:

1. The base is prepared by melting all constituents except talc and cyclomethicone to about 10° C. above their melting points, generally at about 75° C., and blending until homogeneous. Then talc is sprinked in with agitation and the mixture is cooled to 55°–60° C. Thereafter the active PVP-$H_2O_2$ solution is slowly added, followed by cyclomethicone, and the resultant mixture is quickly poured into molds to provide the stick products.

The invention will now be illustrated by the following examples, which should be considered as representative but not limiting of the invention.

PREPARATION OF STABLE, HIGH PURITY, SUBSTANTIALLY ANHYDROUS, FREE-FLOWING 1:1 MOLAR RATIO PVP-$H_2O_2$ COMPLEX (23.4% $_2O_2$)

Example 1

PVP K-15 (GAF Corp. (4.5% water), 111 g., was suspended in 200 ml. of anhydrous ethyl acetate (0.01% $H_2O$), and the suspension was cooled to 0° C. An anhydrous hydrogen peroxide solution in ethyl acetate was prepared by treating 200 g. of 50% aqueous hydrogen peroxide with 6 l. of ethyl acetate, and distilling in a rotary evaporator to remove 100 g. of water from the azeotrope solution. A 42.7% $H_2O_2$ solution in anhydrous ethyl acetate was obtained. Then 100 g. of this solution was slowly added over a period of about 1 ½ hours to the PVP suspension. A fine white precipitate formed which was filtered and dried in vacuo. The resultant water soluble complex contained 23.4% by weight $H_2O_2$ and 0.5% by weight water, upon drying at 50° C. in vacuo for 2 hours.

Example 2

200 g. of PVP (K-30) was suspended in 300 g. of anhydrous ethyl acetate. Then 424 g. of anhydrous $H_2O_2$, (19.6% $H_2O_2$ and 0.84% $H_2O$) in ethyl acetate was added in a 45 minutes period to the cooled (5° C.) suspension of PVP/ethyl acetate. This suspension was stirred for an additional 45 minutes, filtered, and washed with anhydrous ethyl acetate. The resultant fine powder was dried under vacuum at 40°–50° C. for 2 hours to recover residual ethyl acetate. The yield was 258.8 g. of water soluble PVP-$H_2O_2$ complex containing 23.1% $H_2O_2$ and 0.4% $H_2O$, which was a free-flowing, white powder.

Example 3

200 grams of crospovidone XL10 (water-insoluble, cross polymerized PVP) was suspended in 250 g. of anhydrous ethyl acetate. To this suspension 125 g. of anhydrous $H_2O_2$ was added by using 28.1% $H_2O_2$ in anhydrous ethyl acetate and during the addition cooling at 0°–5° C. The resultant, cooled mixture was stirred for an additional 1 hour. The precipitate was filtered to provide 26.2 g. of a water-insoluble, PVP-$H_2O_2$ complex containing 24.1% $H_2O_2$, and 0.5% water, after drying under vacuum at 40° C. for 2 hours.

Stability of Complex of Example 1

After 43 days at 60° C. the complex of Example 1 lost only 15% of its $H_2O_2$ activity, which demonstrates an excellent stability toward decomposition. At room temperature, decomposition was only 1.5% after 60 days.

SUSPENSION PROCESS FOR THE PREPARATION OF FREE-FLOWING, FINE WHITE POWDERS OF 1:1 PVP-$H_2O_2$ COMPLEX

Example 4

PVP-CI (K-30) (GAF Corporation) (4.5% water) was dried at 105° C. in vacuo for 2 hours until it contained only 1.1% water. 160 g. of the dried, water-insoluble PVP was suspended in 450 g. of anhydrous ethyl acetate (0.01% water), and the suspension was cooled to 5°–10° C. while agitating the suspension. Then 55 ml. of 70% hydrogen peroxide solution in water (71 g. $H_2O_2$) was added slowly over a period of 35 minutes to the agitated suspension keeping the temperature at 5°–10° C. A fine, white precipitate was formed which was filtered to yield 312 g. of a wet product which was dried at 40°–50° C. in vacuo for 4 hours. 200 g. of a free-flowing fine, white powder was obtained which contained 19.5% $H_2O_2$ and 2.9% water. Further drying under the same conditions for an additional 6 hours reduced the water content to 0.5% while maintaining the $H_2O_2$ content at 18.5% and without affecting the free-flowing characteristic of the powder.

PROCESS FOR THE PRODUCTION OF 1:1 MOLAR RATIO PVP-H$_2$O$_2$ COMPLEX USING A FLUIDIZED BED REACTOR AND VACUUM DRYING

Example 5

0.35 kg of polyvinylpyrrolidone (PVP K-30, CI grade) having particle sizes of predominantly 40-50 microns, and a moisture content of 2-3%, was introduced into a 0.4 liter fluid bed reactor. The PVP powders were fluidized by passing a stream of dry air upwardly through the charge. The bed temperature was set at 35°-45° C. Then an aqueous solution of 70% H$_2$O$_2$ was metered through a spray nozzle with the assistance of an air stream and directed vertically onto the bed. The rate of addition of the solution was 15-25 g of solution/minute/kg PVP for 20 minutes. Adsorption of the solution onto the bed produced a wet product containing 18% H$_2$O$_2$ and 6% water. Subsequent downstream vacuum drying of the wet material at 25°-35° C. for 10 hours produced a free-flowing powder which had a 20-22% H$_2$O$_2$ content and a water content therein at the same level as the PVP starting material.

PROCESS FOR MAKING 1:1 PVP-H$_2$O$_2$ PRODUCT USING FLUIDIZED BED DRYER

Example 6

3.6 kg of polyvinylpyrrolidone (PVP K-30, CI grade, having a particle size of 40-50 microns, was packed into a 22 liter fluidized bed dryer and fluidized at 35°-45° C. using a dry air stream. Then a 70% H$_2$O$_2$ solution was introduced during 20 minutes at a feed rate of 10-15 g/minute/kg PVP. During the addition, water was being removed continuously from the product and the bed. Following completion of the H$_2$O$_2$ addition, the resultant product was dried further for 10 minutes. The resultant product was a free-flowing powdery complex of PVP-H$_2$O$_2$ having a peroxide content of 20% and a moisture content of only 2%.

Applications of the carrier and effective ingredient also are made to the face of acne patients 2 to 4 times daily with the result that open and closed comedones (blackheads and whiteheads) are markedly reduced within two weeks. The following examples illustrate the present invention.

Example 7

A 1% solution of the PVP-peroxide was prepared in an alcohol-propylene glycol carrier. Twice daily topical application of this solution were self-administered by a 26 year old female patient suffering from acne vulgaris. After two weeks of treatment the comedone count on the patient's face had declined from 28 to 15.

Example 8

A 20 year-old male applied 10% PVP-peroxide prepared in an alcohol gel containing 6% polyoxyethylene lauryl ether four times daily. After 10 days the number of comedones on his face had declined from 43 to 25 and by the end of four weeks of treatment he had only 18 comedones on his face.

Example 9

A 30 year-old female with acne vulgaris applied a 5% by volume solution of PVP-peroxide in a 70% ethyl alcohol and 30% propylene glycol carrier. The product was applied to all involved areas of the face and back twice daily. Before treatment this patient had 64 comedones on the face and back but after two weeks of treatment she had only 41 comedones in these areas.

The preferred composition is clear and stable with 92% hydrogen peroxide remaining after six months' storage at room temperature. Moreover, said composition was found to be effective in reducing the P. Acne causing skin microflora when the composition was tested in a ten (10) day in-vivo antimicrobial study performed on three volunteers in which the composition was applied twice a day to the face area in half face fashion. Skin microflora was obtained on days 2, 3, 5 and 10 and after appropriate incubation under anaerobic conditions, the skin microflora was measured. The reduction in bacteria was determined by comparing the number of microorganisms between the treated and untreated sides of the faces.

Acne is treated in patients by the topical application to the patient of an anti-acne effective amount of the clear stable compositions of this invention.

What is claimed is:

1. A composition for treating acne vulgaris consisting essentially of about 1 to 10% by weight of active H$_2$O$_2$ provided by a stable, high purity, substantially anhydrous, 1:1 molar ratio complex of PVP and H$_2$O$_2$ in the form of a free-flowing, fine white powder in a non-aqueous, organic solvent.

2. A composition according to claim 1 which is a stick formulation which includes a base component therein.

3. A composition according to claim 2 wherein the complex and solvent, and base, are present in amounts of 40-60:60-40, respectively.

4. A composition according to claim 1 wherein said organic solvent is ethanol, propylene glycol or glycerol.

5. A composition according to claim 4 wherein said complex to solvent weight ratio is about 60:40, 50:50 and 25-30:70-75, respectively.

6. A method for treating acne vulgaris which comprises contacting living tissue affected with the composition of claim 1.

7. A method according to claim 6 wherein said active H$_2$O$_2$ is present in said composition at about a 3 to 7% by weight level.

8. A method according to claim 6 wherein said composition is a stick formulation which includes a base component.

9. A method according to claim 8 wherein said complex in said non-aqueous, organic solvent, and said base component, are present in amount of 40-60:60:40, respectively.

* * * * *